United States Patent

Kirrstetter et al.

[11] Patent Number: 4,692,516
[45] Date of Patent: * Sep. 8, 1987

[54] PROCESS FOR THE MANUFACTURE OF 3-PYRIDINIUM-METHYL-CEPHALOSPORINS

[75] Inventors: Reiner Kirrstetter, Kelkheim; Walter Dürckheimer, Hattersheim am Main; Rudolf Lattrell, Königstein/Taunus; Wilfried Schwab, Kelkheim, all of Fed. Rep. of Germany

[73] Assignee: Hoechst Aktiengesellschaft, Fed. Rep. of Germany

[*] Notice: The portion of the term of this patent subsequent to May 19, 2004 has been disclaimed.

[21] Appl. No.: 607,593

[22] Filed: May 7, 1984

[30] Foreign Application Priority Data

May 7, 1983 [DE] Fed. Rep. of Germany ....... 3316797

[51] Int. Cl.$^4$ .......................................... C07D 501/46
[52] U.S. Cl. .................................. 540/222; 540/225; 540/227
[58] Field of Search ........................... 544/22, 25, 27; 540/222, 225, 227

[56] References Cited

U.S. PATENT DOCUMENTS 4,258,041  3/1981  O'Callaghan .................. 544/22
4,266,049  5/1981  Bonjouklian .................. 544/16
4,382,932  5/1983  Lunn ............................ 544/22
4,396,620  8/1983  Lunn ............................ 544/22

FOREIGN PATENT DOCUMENTS 0060144  3/1982  European Pat. Off. .
0070706  7/1982  European Pat. Off. .

Primary Examiner—Robert J. Warden
Assistant Examiner—Robert Benson
Attorney, Agent, or Firm—Finnegan, Henderson, Farabow, Garrett & Dunner

[57] ABSTRACT

Process for the preparation of cephem compounds of the formula

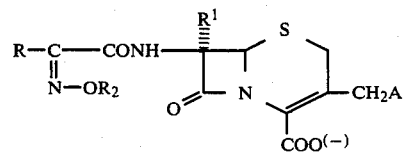

wherein R is optionally substituted aminothiazolyl or amino-1,2,4-thiadiazolyl, A is optionally substituted pyridinium, $R^1$ is hydrogen or methoxy and $R^2$ are special aliphatic substituents, by a nucleophilic replacement in the substituent in 3-position in the presence of tri-$C_1C_4$-alkyl iodosilane.

2 Claims, No Drawings

PROCESS FOR THE MANUFACTURE OF 3-PYRIDINIUM-METHYL-CEPHALOSPORINS

The invention relates to a process for the preparation of cephem compounds of the general formula I

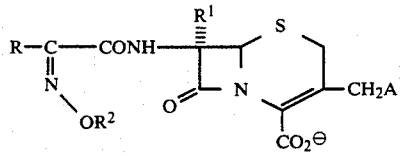

in which R denotes a thiazolyl radical

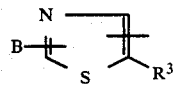

or a 1,2,4-thiadiazolyl radical

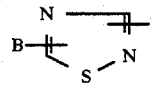

in which
$R^3$ represents hydrogen or halogen and B represents an optionally substituted amino group, and wherein
$R^1$ denotes hydrogen or methoxy,
$R^2$ denotes hydrogen, optionally substituted $C_1$–$C_6$-alkyl, optionally substituted $C_2$–$C_6$-alkenyl, $C_2$–$C_6$-alkinyl, $C_3$–$C_7$-cycloalkyl, $C_3$–$C_7$-cycloalkyl-$C_1$–$C_6$-alkyl, $C_4$–$C_7$-cycloalkenyl or the group

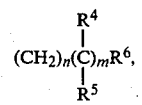

in which m and n are each 0 or 1,
$R^4$ and $R^5$ can be identical or different and denote hydrogen, aryl or a $C_1$–$C_4$-alkyl group, or, together with the carbon to which they are bonded, form a methylene or $C_3$–$C_7$-cycloalkylidene group, it being possible for the $C_1$–$C_4$-alkyl and the $C_3$–$C_7$-cycloalkylidene group also to be further monosubstituted or polysubstituted, and
$R^6$ denotes a COOH, CN or $CONH_2$ group, it being possible for the latter to be monosubstituted or disubstituted on the nitrogen, and
A denotes a quinolinium

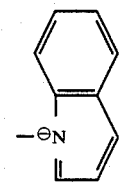

or an isoquinolinium

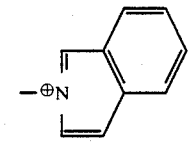

radical, each of which can also be monosubstituted or polysubstituted by identical or different substituents from the group comprising optionally substituted $C_1$–$C_6$-alkyl, $C_1$–$C_6$-alkoxy, halogen, trifluoromethyl and hydroxyl, or denotes a phenanthridinium radical, or denotes a pyridinium radical

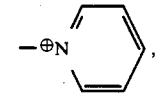

which can be monosubstituted or polysubstituted by identical or different substituents from the group comprising optionally substituted $C_1$–$C_6$-alkyl, it being possible for 2 alkyl groups in the ortho-position also to be linked to form an optionally substituted di- to deca-methylene ring in which one ring carbon atom can be replaced by a heteroatom and which can furthermore also contain one or two double bonds; optionally substituted $C_2$–$C_6$-alkenyl, $C_2$–$C_6$-alkinyl, $C_3$–$C_7$-cycloalkyl and $C_3$–$C_7$-cycloalkylmethyl, it being possible for the ring in these last two substituents also to be substituted; $C_4$–$C_7$-cycloalkenyl, optionally substituted $C_1$–$C_6$-alkoxy, $C_2$–$C_6$-alkenyloxy and $C_2$–$C_6$-alkinyloxy, halogen, trifluoromethyl and hydroxyl, optionally substituted phenyl, benzyl and heteroaryl, formyl and ketalized formyl, optionally substituted $C_1$–$C_6$-alkylcarbonyl, which can also be in ketalized form, arylcarbonyl and carbamoyl,
and in which the $R^2O$ group is in the syn-position.

The present invention particularly relates to compounds
in which
R and $R^1$ have the above meanings,
B denotes an amino group, which can be substituted by amino-protected groups,
$R^2$ denotes hydrogen, $C_1$–$C_6$-alkyl, which can be monosubstituted or polysubstituted by halogen, $C_1$–$C_6$-alkylthio, $C_1$–$C_6$-alkoxy, aryl or heteroaryl, or denotes $C_2$–$C_6$-alkenyl, which can be monosubstituted or polysubstituted or halogen; or denotes $C_2$–$C_3$-alkinyl, $C_3$–$C_6$-cycloalkyl, $C_3$–$C_6$-cycloalkyl-$C_1$–$C_6$-alkyl, $C^4$–$C_7$-cycloalkenyl, and in which the group

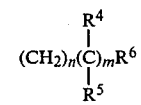

has the above meaning, and
A denotes a quinolinium or isoquinolinium radical, each of which can also be monosubstituted or polysubstituted by identical or different substituents from the group comprising
$C_1$–$C_6$-alkyl, which can be substituted or hydroxyl;
$C_1$–$C_6$-alkoxy,
halogen,
trifluoromethyl and hydroxyl,
or denotes a pyridinium radical

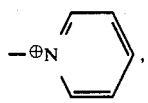

which can be monosubstituted or polysubstituted by identical or different substituents from the group comprising $C_1$–$C_6$-alkyl, which can be monosubstituted or polysubstituted by hydroxyl; formyl and $C_1$–$C_6$-alkylcarbonyl, the carbonyl groups of which can also be in ketalized form, sulfo, carbamoyl, $C_1$–$C_6$-alkoxy and hydroxy-$C_1$–$C_6$-alkoxy, it also being possible for 2 alkyl groups to be linked to form an optionally substituted di- to deca-methylene ring in which one ring carbon atom can also be replaced by a heteroatom and which can furthermore also contain one or two double bonds, $C_2$–$C_6$-alkenyl, which can be substituted by hydroxyl,
$C_2$–$C_6$-alkinyl,
$C_3$–$C_7$-cycloalkyl and $C_3$–$C_7$-cycloalkylmethyl, it being possible for the ring in these two substituents also to be substituted by hydroxyl or halogen,
$C_4$–$C_7$-cycloalkenyl,
$C_1$–$C_6$-alkoxy, which can be substituted by hydroxyl,
$C_2$–$C_6$-alkenyloxy and $C_2$–$C_6$-alkinyloxy,
halogen, trifluoromethyl and hydroxyl, phenyl, benzyl and heteroaryl, which can also be substituted by halogen,
formyl and ketalized formyl,
$C_1$–$C_6$-alkylcarbonyl, which can also be substituted by hydroxyl and can also be in ketalized form,
arylcarbonyl and
carbamoyl, and in which, in these preferred compounds falling within the general formula I, the $R^2O$ group is also in the syn-position.

Possible optional substituents of the di- or decamethylene ring mentioned under A, in which one ring carbon atom can be replaced by a heteroatom and which can furthermore also contain one or two double bonds, are, in particular, the following substituents, which may occur individually or in combination, but preferably individually: $C_1$–$C_6$-alkyl, $C_1$–$C_4$-alkoxy, hydroxymethyl, halogen, hydroxyl, oxo and exomethylene.

These substituents may occur on the above rings fused onto the pyridinium radical, independently of whether the particular ring is saturated, unsaturated or interrupted by a heteroatom.

The ring fused onto the pyridinium radical can contain 2 to 10 ring members (di- to deca-methylene), but preferably 3 to 5 ring members, and thus can be, for example, a cyclopenteno, cyclohexeno or cyclohepteno ring. If such a fused-on ring contains a double bond, examples which may be mentioned are the dehydrocyclopentadieno, dehydrocyclohexadieno and dehydrocycloheptadieno ring. If a carbon atom in such rings is replaced by a heteroatom, possible heteroatoms are, in particular, oxygen and sulfur. Examples which may be mentioned of fused-on rings which contain an oxygen atom and one or two double bonds are furo, pyrano, dihydrofuro and dihydropyrano; possible fused-on rings which contain a sulfur atom and one or two double bonds are thieno, thiopyrano, dihydrothieno and dihydrothiopyrano. Of the fused-on rings containing a heteroatom, those rings which contain only one double bond are particularly suitable for substitution, in particular by the abovementioned substituents.

Examples of particularly preferred substituents are the following:

B: $NH_2$, $HCONH$, $CF_3CONH$, $CCl_3CONH$, $C_6H_5CH_2CONH$, $(C_6H_5)_3CNH$, $HSO_3NH$ and $(CH_3)_2CH=N$,

R:

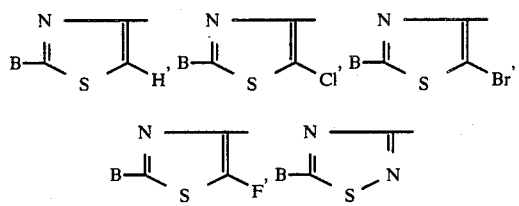

$R^1$: hydrogen and $OCH_3$ $R^2$: hydrogen, $C_1$–$C_6$-alkyl, such as, for example methyl, ethyl, propyl, isopropyl and butyl, preferably methyl and ethyl; $C_1$–$C_2$-halogenoalkyl, for example alkyl which is substituted by chlorine, bromine, iodine or fluorine, preferably trifluoroethyl, difluoromethyl and 2,2,3,3-tetrafluoropropyl, alkyl which is substituted by aryl, such as, for example, phenyl, tolyl and chlorophenyl, in particular benzyl, alkyl which is substituted by heteroaryl, such as, for example, 1,3-thiazol-4-yl-substituted alkyl, in particular 1,3-thiazol-4-yl-methyl, $C_2$–$C_6$-alkenyl, such as, for example, vinyl, allyl, isopropenyl and methallyl, in particular allyl and methallyl, $C_2$–$C_6$-alkenyl which is substituted by halogen, such as, for example, chlorine or bromine, in particular 3-chloropropen-2-yl, 2-bromopropen-2-yl and 2-chloropropen-2-yl;

$C_2$–$C_3$-alkinyl, such as, in particular, propargyl, $C_3$–$C_7$-cycloalkyl, such as, in particular, cyclopropyl, cyclobutyl and cyclopentyl, $C_3$–$C_7$-cycloalkyl-$C_1$–$C_6$-alkyl, such as, in particular, cyclopropylmethyl and cyclobutylmethyl, $C_4$–$C_7$-cycloalkenyl, such as, in particular, cyclopenten-1-yl, and the group

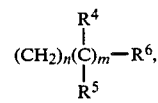

in which $R^4$ and $R^5$ can be identical or different and can denote hydrogen, aryl, preferably phenyl, or $C_1$–$C_4$-alkyl, such as, for example, methyl, ethyl, propyl, isopropyl, butyl or sec.-butyl, preferably methyl or ethyl, and in particular methyl, or in which $R^4$ and $R^5$, together with the carbon atom to which they are bonded, can form a methylene group or a $C_3$–$C_7$-cycloalkylidene group, such as, for example, cyclopropyl, cyclobutyl, cyclopentyl, cyclohexyl or cycloheptyl, preferably cyclopropyl, cyclobutyl, cyclopentyl or cyclohexyl, it being possible for the cycloalkylidene group to be substituted, for example by $C_1$–$C_4$-alkyl, preferably methyl, by halogen, preferably fluorine and chlorine, or by alkylene with 3-6 carbon atoms, m=0 or 1 and n=0 or 1, the sum of m and n being 1 or 2.

Preferred examples of the group

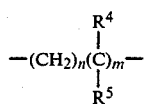

are the following:

If n=0 and m=1:

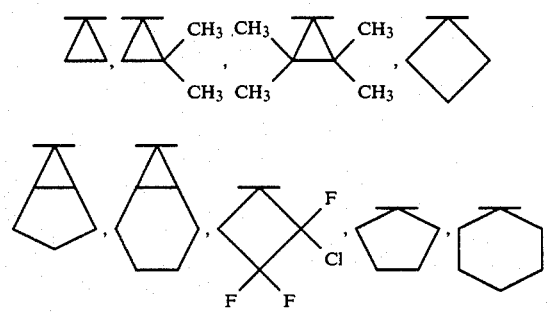

and if m=0 and n=1: —CH$_2$—, and if n and m=1: —CH$_2$—C(=CH$_2$)—.

R$^6$: the COOH, CN and CONH$_2$ groups, and carbamoyl which is substituted by C$_1$-C$_6$-alkyl, preferably methy or ethyl.

A: a quinolinium or an isoquinolinium radical, each of which can also be monosubstituted or polysubstituted by identical or different substituents from the group comprising C$_1$-C$_6$-alkyl, such as, for example, methyl, ethyl, propyl and isopropyl, preferably methyl, methoxy, hydroxyl, halogen and trifluoromethyl, or a pyridinium radical, which can be monosubstituted or polysubstituted, preferably mono-, di- or tri-substituted, in particular mono- or di-substituted, for example by C$_1$-C$_4$-alkyl, such as, in particular, methyl, ethyl, propyl, isopropyl, n-butyl, sec.-butyl, tert.-butyl, dimethyl, trimethyl, methyl and ethyl, methyl and propyl, methyl and isopropyl or ethyl and ethyl;

hydroxy-C$_1$-C$_4$-alkyl, such as, in particular, hydroxymethyl, hydroxyethyl, hydroxypropyl, hydroxyisopropyl, hydroxybutyl, hydroxy-sec.-butyl or hydroxy-tert.-butyl, it also being possible, for example, for the alkyl radical to carry two or three hydroxyl groups; formyl-C$_1$-C$_4$-alkyl, such as, in particular, formylmethyl, C$_1$-C$_4$-alkylcarbonyl-C$_1$-C$_4$-alkyl, such as, in particular, methylcarbonylmethyl, ethylcarbonylmethyl, methylcarbonylethyl and ethylcarbonylethyl; C$_3$-C$_4$-alkenyl, such as, in particular, allyl, 2-methallyl and buten-3-yl, which can also be substituted by hydroxyl, such as, in particular, hydroxyallyl and hydroxybutenyl; C$_3$-alkinyl, such as, in particular, propargyl; C$_3$-C$_6$-cycloalkyl and C$_3$-C$_6$-cycloalkyl-methyl, the carbon number relating to the cycloalkyl part, such as, in particular, cyclopropyl, cyclobutyl, cyclopentyl, cyclohexyl and cyclopentylmethyl, it also being possible for the rings to be substituted, for example by hydroxyl, such as, in particular, 1-hydroxy-1-cyclopentyl and 1-hydroxy-1-cyclohexyl, or by halogen, preferably chlorine;

C$_5$-C$_6$-cycloalkenyl, such as, in particular, cyclopenten-1-yl and cyclohexen-1-yl;

C$_1$-C$_6$-alkoxy, such as, in particular, methoxy and ethoxy, halogen, such as, in particular, 3-fluoro, 3-chloro, 3-bromo or 3-iodo; hydroxyl, in particular 3-hydroxy; trifluoromethyl, in particular 3-trifluoromethyl; phenyl and benzyl, which can also be substituted, for example by halogen, in particular chlorine, such as, for example, 4-chlorobenzyl; 2'-thienyl and 3'-thienyl; C$_1$-C$_4$-alkylcarbonyl, in particular acetyl and propionyl, preferably acetyl; and formyl, benzoyl and carbamoyl.

If A is a pyridinium radical which is substituted by two alkyl groups linked to form a di- to deca-methylene ring, which in turn can be monosubstituted or polysubstituted, preferably monosubstituted, and can contain one or two double bonds, the following fused-on ring systems are very particularly suitable here:

Cyclobuteno, cyclopenteno, hydroxycyclopenteno, oxocyclopenteno, hydroxymethylcyclopenteno, exomethylencyclopenteno, carboxycyclopenteno and carbamoyl-cyclopenteno, cyclohexeno, hydroxycyclohexeno, oxocyclohexeno, hydroxymethylcyclohexeno, exomethylenecyclohexeno, carboxycyclohexeno and carbamoylcyclohexeno, cyclohepteno, hydroxy-, oxo-, hydroxymethyl-, exo- methylene- and carboxy-cyclohepteno and carbamoylcycloheptno; and dehydro-cyclopenteno, dehydrocyclohexeno and dehydro-cycloheptno.

If a ring carbon atom in the abovementioned fused-on ring systems is replaced by a heteroatom, in particular oxygen or sulfur, particularly suitable ring systems are:

Furo[2,3-b]pyridine, furo[3,2-b]pyridine, furo[2,3-c]pyridine, furo[3,2-c]pyridine, thieno[2,3-b]pyridine, thieno[3,2-b]pyridine, thieno[2,3-c]pyridine, thieno[3,2-c]pyridine, thieno[3,4-b]pyridine and thieno[3,4-c]pyridine.

The process, according to the invention, for the preparation of compounds of the formula I comprises reacting a compound of the general formula II

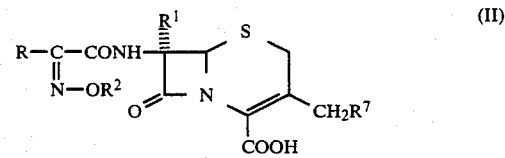

or salts thereof, in which R, R$^1$ and R$^2$ have the meaning given for formula I and R$^7$ denotes a group which can be replaced by the base corresponding to the radicals A of formula I, with this base in the presence of a tri-C$_1$-C$_4$-alkyliodosilane, preferably trimethyl- or triethyliodosilane, and (a) splitting off any protective group present and (b) if necessary, converting the resulting product into a physiologically acceptable acid addition salt.

The use of trimethyliodosilane is particularly preferred.

Possible radicals R$^7$ are, in particular, acyloxy radicals of lower aliphatic carboxylic acids, preferably with 1 to 4 carbon atoms, such as, for example, acetoxy or propionyloxy, in particular acetoxy, which can optionally be substituted, such as, for example, chloroacetoxy or acetylacetoxy. Other groups, such as, for example, carbamoyloxy, are also possible for R$^7$.

The starting compounds are known from the literature or they can be prepared by processes which are known from the literature (cf. for example German Offenlegungsschrift No. 2,716,707, German Offenlegungsschrift No. 3,118,732 and German Patent Application Nos. P 32 07 840, P 32 47 613 and P 32 47 614).

It is known from European Pat. No. 64,740 and No. P 32 07 840.4 that compounds of the general formula I in which R denotes a 2-aminothiazol-4-yl radical and their physiologically acceptable salts have excellent antibacterial activities both against Gram-positive and against Gram-negative bacterial germs. These compounds can be prepared, for example, from compounds of the general formula II by direct reaction with the corresponding bases, preferably in water or aqueous mixtures as the solvent. It is also reported in the literature (European Pat. No. 60,144) that 3-iodomethyl-cephalosporin derivatives, for example compounds which correspond to the formula I with $A=I$, react with pyridine bases to give the corresponding pyridinium compounds. Such iodoalkyl compounds can generally be prepared from esters, for example acetates, with trimethyliodosilane (J. Amer. Chem. Soc. 99, 968, 1977; and Angew. Chemie 91, 648, 1979), a reaction which has subsequently been applied to cephalosporins (cf. European Pat. No. 34,924, U.S. Pat. No. 4,266,049, Tetrahedron Letters 1981, 3915 and European Pat. No. 70,706 (Example 5)).

In the two-stage process described in European Pat. No. 60,144, for example, the acetates corresponding to the formula II ($R^7=OCOCH_3$) are first converted into the 3-iodomethyl compounds, and these are isolated and then reacted with the desired pyridine bases. Purification by chromatography is necessary for isolation of the end products. The maximum yield of pure end product is less than 10% of theory.

Surprisingly, it has now been found that the yields of end products of the formula I are increased decisively up to more than ten-fold by the process according to the invention if the nucleophilic replacement reaction is carried out from the start in the presence of an excess of the corresponding bases on which the radical A in formula I is based, i.e. a tri-$C_1$–$C_4$-alkyliodosilane, preferably trimethyliodosilane, is added to the reaction mixture after the addition of the base.

The process is carried out by adding the base corresponding to the radical A to a solution or suspension of the compound II in a suitable solvent, and then adding trimethyliodosilane. Instead of trimethyliodosilane, it is also possible to use, for example, a reaction mixture of iodine and hexamethyldisilane, which has first been reacted at temperatures between about 60° and 120° C. in a manner which is known from the literature, trimethyliodosilane being formed. The same good result can also be obtained by using triethyliodosilane, which is prepared in a manner which is known from the literature, instead of trimethyliodosilane.

The reaction is carried out at temperatures between about $-5°$ and $+100°$ C., preferably between $+10°$ and $+80°$ C.

Examples of suitable inert aprotic solvents are chlorinated hydrocarbons, such as methylene chloride, chloroform, dichloroethane, trichloroethane and carbon tetrachloride, lower alkyl-nitriles, such as acetonitrile or propionitrile, or frigands or toluene; in particular, methylene chloride is an outstanding solvent.

The base corresponding to the radical A is added in at least the stoichiometric amount up to a twenty-fold excess, and amounts which bond the quantity of hydrogen iodide liberated and leave at least 1 mole, preferably 2-5 moles, of the base available for substitution are preferably used.

Since, besides the group $R^7$ to be replaced, other functional groups in the starting compound II, such as amino, carboxyl or amide groups, also react with trimethyliodosilane, the latter is added in at least a four-fold up to about a twenty-fold excess, preferably in a five- to ten-fold excess.

The process for forming the cephalosporins of the formula I can also be carried out in the form of adding a mixture of a base corresponding to radical A and trimethyliodosilane to a suspension of compound II in a suitable solvent, such as, for example, methylene chloride, or also vice versa, and then allowing the reaction to take place. In a further variant, the reaction after the reactants have been added together in the ways described above can be carried out at temperatures between 10° and 100° C. in a sealed system, such as, for example, an autoclave. The reaction product is worked up in the conventional manner after it has cooled down to 0°-20° C. and air has been let into the sealed system.

Carboxyl and N-amino groups in the compound II can also be pre-silylated by addition of a silylating agent, such as, for example, bistrimethylsilylacetamide, bistrimethylsilyltrifluoroacetamide, trimethylchlorosilane, hexamethyldisilazane or bistrimethylsilylurea, either in the absence of or in the presence of a base, preferably the desired base on which the group A is based, in the amounts described above. At least the stoichiometric amount or an excess, preferably a two-fold to ten-fold excess of trimethyliodesilan is then added.

If the base on which the radical A in formula I is based contains functional groups, such as, for example, hydroxyl groups and the like, these are preferably presilylated with one of the abovementioned silylating agents and then used in the reaction.

The reaction products of the formula I can be isolated, for example, from the aqueous phase, obtained by adding water or aqueous mineral acids, for example dilute HCL, HBr, HI or $H_2SO_4$, in the customary manner, for example by freeze-drying the aqueous phase, chromatography and the like. The polar reaction products are preferably precipitated out of the reaction solution in the form of sparingly soluble salts by adding aqueous mineral acids, such as, for example, HCL, HBr, HI or $H_2SO_4$, which have been dissolved in alcohols, such as, for example, methanol, ethanol, propanol, isopropanol, butanol, isobutanol or acetone or mixtures thereof.

These are then converted into physiologically acceptable acid addition salts by processes which are known from the literature, for example according to Patent Application No. P 32 48 828.7 (Patent).

The following embodiment examples for the compounds which can be prepared by the process according to the invention serve to further illustrate the invention, but without limiting it thereto.

EXAMPLE 1

7-[2-(2-Aminothiazol-4-yl)-2-syn-methoxyiminoacetamido]-3-[(2,3-cyclopenteno-1-pyridinio)-methyl]-ceph-3-em-4-carboxylate dihydriodide Variant a:

100 ml (0.85 mole) of 2,3-cyclopentenopyridine followed by 140 g (100 ml, 0.7 mole) of trimethyliodosilane are added to a mixture of 45.5 g (0.1 mole of 7-[2-(2-aminothiazol-4-yl)-2-syn-methoxyiminoacetamido]-cephalosporanic acid and 900 ml of methylene chloride. The reddish brown-coloured solution is kept under reflux for 2 hours and then cooled to −15° C., and a solution of 60 g of potassium iodide in 250 ml of 2N HCl is added, while shaking. A precipitate forms, and the mixture is left in an ice-bath for 2 hours, with occasional shaking, and then in a refrigerator overnight. The yellow precipitate is filtered off with suction and stirred with three 100 ml portions of ice-water in a glass beaker, being filtered off with suction each time. The moist product is then introduced into 500 ml of acetone, while stirring, and is filtered off with suction and washed with three 100 ml portions of acetone. After drying in vacuo over $H_2SO_4$, 54.5 g (69% of theory) of light yellow-coloured crystals of decomposition point 179°–181° C. are obtained.

$C_{22}H_{22}N_6O_5S_2 \times 2HI \times H_2O$ (788.43) Calculated: C 33.51 H 3.32 I 32.19 N 10.66 S 8.13 $H_2$ 2.3% Found: C 33.6 H 3.6 I 31.3 N 10.7 S 7.1 $H_2$ 2.5%

IR (KBr): 1785 cm$^{-1}$ (lactam CO).

$^1$HR—NMR (CF$_3$CO$_2$D): δ=2.30–2.85 (m, 2H, cyclopentene H); 3.10–4.05 (m, 6H, 4 cyclopentene H and SCH$_2$); 4.41 (s, 3H, OCH$_3$); 5.25–6.23 (m, 4H, CH$_2$Py and 2 Lactam H); 8.11 (s, 1H, thiazole); and 7.65–8.70 ppm (m, 3H, Py).

Variant b:

58.5 g (82 ml, 0.4 mole) of hexamthyldisilane are heated to 70°–75° and 88.8 g (0.7 mole) of iodine are added in portions in the course of 20 minutes. After the addition of iodine, the mixture is kept under reflux for 30 minutes, cooled to 10° and diluted with 900 ml of methylene chloride. 100 ml (0.85 mole) of 2,3-cyclopentenopyridine, followed by 45.5 g (0.1 mole) of 7-[2-(2-aminothiazol-4-yl)-2-syn-methoxyiminoacetamido]-cephalosporanic acid, are then added. The mixture is heated under reflux for 2 hours and then hydrolyzed as above with KI/2N HCl. The precipitate formed is isolated as described in variant a. Yield: 57.5 g (73% of theory) of the light yellow dihydriodide salt. The compound is identical in all its properties to that described above.

Variant c:

3.2 ml (20 mmoles) of triethysilane are added to a solution of 4.6 g (36 mmoles) of iodine in 35 ml of methylene chloride and the solution is heated under reflux for 30 minutes. It is cooled, and 1.45 ml (12 mmoles) of 2,3-cyclopentenopyridine followed by 0.91 g (2 mmoles) of 7-[2-(2-aminothiazol-4-yl)-2-syn-methoxyiminoacetamido]cephalosporanic acid are added. The reddish brown-colored solution is heated under reflux for 2 hours, cooled to −20° C. and hydrolyzed by adding a solution of 2 g of potassium iodide in 10 ml of 2N HCl. The mixture is stirred in an ice-bath for 4 hours and left in a refrigerator overnight, and the precipitate is filtered off with suction and washed with three 5 ml portions of ice-water and three 10 ml portions of acetone. After drying, 1.1 g (70% of theory) of light yellow crystals are obtained.

The compound is identical in all its properties to that described under variant a.

EXAMPLE 2

3-[2,3-Cyclopenteno-1-pyridinio)methyl]-7-[2-syn-methoxyimino-2-(2-phenylacetamidothiazol-4-yl)acetamido]-ceph-3-em-4-carboxylate hydriodide The title compound is obtained from 0.86 g (1.5 mmoles) of 7-[2-syn-methoxyimino-2-(2-phenylacetamidothiazol-4-yl)acetamido]-cephalosporanic acid, 1.1 ml (9 mmoles) of 2,3-cyclopentenopyridine and 1.1 ml (7.5 mmoles) of trimethyliodosilane in 35 ml of methylene chloride analogously to Example 1a. After the hydrolysis with 40 ml of 2N HCl at 5°, the yellow precipiate which has separated out is filtered off with suction, washed with a little ice-water and dried over $P_2O_5$.

Yield: 1.0 g (88% of theory) of light yellow solid.

IR (KBr): 1785 cm$^{-1}$ (lactam CO)

$^1$H—NMR (D$_6$—DMSO): δ=1.8–2.4 (m, 2H, cyclopentene H); 2.8–3.5 (m, 6H, 4 cyclopentene H and SCH$_2$); 3.72 (s, 2H, CH$_2$—CO); 3.83 (s, 3H, OCH$_3$); 5.17 (d, 1H, lactam H); 5.48 (broad s, 2H, (CH$_2$Py)); 5.85 (q, 1H, lactam H); 7.27 (s, 5H, C$_6$H$_5$); 7.5–8.8 (m, 4H, Py and thiazole); 9.67 (d, 1H, NH); and 12.70 ppm (s, 1H, NH).

EXAMPLE 3

3-[(2,3-Cyclopenteno-1-pyridinio)methyl]-7-[2-syn-methoxyimino-2-(2-tritylaminothiazol-4-yl)acetamido]-ceph-3-em-4-carboxylate hydriodide The title compound is obtained from 1.16 g (1.5 mmoles) of 7-[2-syn-methoxyimino-2-(2-tritylaminothiazol-4-yl)acetamido]-cephalosporanic acid, 1.1 ml (9 mmoles) of 2,3-cyclopentenopyridine and 1.1 ml (7.5 mmoles) of trimethyliodosilane in 35 ml of methylene chloride analogously to Example 1a. After hydrolysis with 40 ml of 2N HCl at 5°, the methylene chloride is removed on a rotary vacuum evaporator, the aqueous phase is decanted off from an oily residue and the residue is stirred with 40 ml of water at 0°–5° for 2 hours. The precipitate formed is filtered off with suction, washed with ice-water and dried over $P_2O_5$.

Yield: 1.24 g (93% of theory) of yellow solid.

IR (KBr): 1785 cm$^{-1}$ (lactam CO)

$^1$H—NMR (D$_6$—DMSO): δ=1.8–2.4 (m, 2H, cyclopentene H); 2.9–3.5 (m, 6H, 4 cyclopentene H and SCH$_2$); 3.80 (s, 3H, OCH$_3$); 5.16 (d, 1H, lactam H); 5.50 (broad s, 2H, CH$_2$Py); 5.74 (q, 1H, lactam H); 6.70 (s, 1H, thiazole); 7.30 (s, 15H, C$_6$H$_5$); 7.7–8.8 (m, 3H, Py); 9.0 (broad s, 1H, NH); and 9.58 ppm (d, 1H, NH).

EXAMPLE 4

7-[2-(2-Aminothiazol-4-yl)-2-syn-methoxyiminoacetamido]-3-(1-pyridiniomethyl)-ceph-3-em-4-carboxylate dihydriodide The title compound is obtained from 4.55 g (10 mmoles) of 7-[2-(2-aminothiazol-4-yl)-2-syn-methoxyiminoacetamido]-cephalosporanic acid, 6.8 ml (8.5 mmoles) of pyridine and 10 ml (70 mmoles) of trimethyliodosilane in 100 ml of methylene chloride analogously to Example 1a. After cooling, the red-brown solution is hydrolyzed with a solution of 10 g of KI in 50 ml of 2N HCl, and the mixture is stirred in an ice-bath for 4 hours and left in a refrigerator overnight. The precipitate is filtered and washed four times with a little ice-water. After drying over $P_2O_5$, 4.5 g (61% of theory) of the title compound are obtained in the form of a yellow solid.

IR (KBr): 1783 cm$^{-1}$ (lactam CO)

$^1$H—NMR (CF$_3$CO$_2$D): δ=3.53 and 3.95 (AB, J=19 Hz, 2H, SCH$_2$); 4.40 (s, 3H, OCH$_3$); 5.2–6.4 (m, 4H, CH$_2$Py and 2 lactam H); and 7.9–9.3 ppm (m, 6H, Py and thiazole).

EXAMPLE 5

7-[2-(2-Aminothiazol-4-yl)-2-syn-methoxyiminoacetamido]-3-(5-phenanthridiniomethyl)-ceph-3-em-4-carboxylate dihydriodide A mixture of 0.91 g (2 mmoles) of 7-[2-(2-aminothiazol-4-yl)-2-syn-methoxyiminoacetamido]-cephalosporanic acid, 2.87 g (16 mmoles) of phenanthridine and 2 ml (14 mmoles) of trimethyliodosilane in 20 ml of methylene chloride is heated under reflux for 2 hours. The mixture is cooled, a yellow crystalline precipitate of phenanthridine hydriodie is filtered off with suction and the filtrate is concentrated in vacuo. A precipate thereby forms, and is filtered off with suction and washed successively with methylene chloride, water and ether. After drying over $P_2O_5$, 930 mg (81% of theory) of the title compound are obtained in the form of light yellow crystals.

IR/KBr: 1785 $cm^{-1}$ (lactam CO)

$^1$H—NMR ($CF_3CO_2D$): δ=3.47 and 3.73 (AB, J=18 Hz, 2H, $SCH_2$); 4.48 (s, 3H, $OCH_3$); 5.25 and 6.40 (AB, J=7 Hz, 2H, $CH_2$-phenanthridine); 5.40 and 6.03 (AB, J=5 Hz, 2H, 2 lactam H); 7.90–8.70 (m, 7H, phenanthridine and thiazole); 8.80–9.30 (m, 2H, 1H and 10H of phenanthridine); and 9.88 ppm (s, 1H, 6H of phenanthridine).

The compounds shown below are obtained in the form of the free bases, which correspond to the general formula I', analogously to Example 1, variant a.

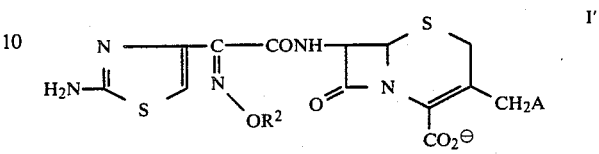

The crude hydriodide salts obtained after hydrolysis of the reaction solution are dissolved, with addition of sodium bicarbonate, and chromatographed over silica gel (Merck 0.063—0.2 mm) using acetone:water (3:1). After freeze-drying the product fractions, the compounds of Examples 6–20 are obtained in amorphous form.

TABLE 1

Compounds

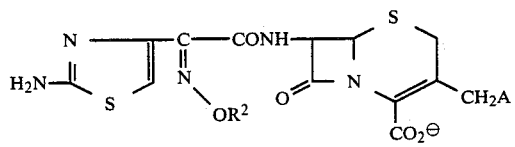

| Example | $R^2$ | A | Yield % of theory | $^1$H—NMR($CF_3CO_2D$): δ(ppm) |
|---|---|---|---|---|
| 6 | $C_2H_5$ | 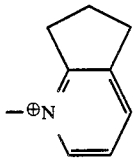 | 20 | 1.43 (t, J = 7Hz, 3H, $CH_2CH_3$); 2.2–2.8 (m, 2 cyclopentene H); 3.05–3.95 (m, 6H, 4 cyclopentene H and $SCH_2$); 4.51 (q, J = 7Hz, 2H, $CH_2CH_3$), 5.05–6.26 (m, 4H, $CH_2$Py and 2 lactam H); 7.42 (s, 1H, thiazole); and 7.5–8.7 (m, 3H, Py). |
| Example | $R^2$ | A | Yield % of theory | $^1$H—NMR in $CF_3CO_2D$: δ(ppm) |
| 7 | $C_3H_7$ | 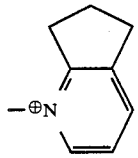 | 46 | 1.08 (t, J = 6Hz, 3H, $CH_3$); 1.6–2.8 (m, 4H, $CH_2$ and 2 cyclopentene H); 3.1–4.2 (m, 6H, 4 cyclopentene H and $SCH_2$); 4.53 (t, J = 6Hz, $OCH_2$); 5.1–6.3 (m, 4H, $CH_2$Py and 2 lactam H); 7.42 (s, 1H, thiazole); and 7.4–8.5 ppm (m, 3H, Py) |
| 8 | $CH(CH_3)_2$ | 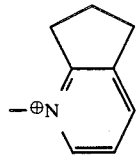 | 37 | 1.47 and 1.57 (d, J = 6Hz, 6H, 2 $CH_3$); 2.1–2.8 (m, 2H, cyclopentene H); 3.0–4.2 (m, 6H, 4 cyclopentene H and $SCH_2$); 4.8 (m, 1H, CH); 5.1–6.4 (m, 4H, $CH_2$Py and 2 lactam H); 7.41 (s, 1H, thiazole); and 7.5–8.6 ppm (m, 3H, Py). |

TABLE 1-continued

Compounds

[Structure: H2N-C(=N)-S-thiazole-C(=N-OR²)-CONH-β-lactam-CH2A, CO2⁻]

| No. | R² | A | Yield | NMR |
|---|---|---|---|---|
| 9 | CH₃ | –⁺N(quinolinium) | 36 | 3.40 and 3.80 (AB, J = 19Hz, 2H, SCH₂); 4.21 (s, 3H, OCH₃); 5.30–6.50 (m, 4H, 3-CH₂ and 2 lactam H each with 1 d at 5.41 and 6.10, J = 5Hz, C₆ and C₇—H); 7.42 (s, 1H, thiazole); 7.95–8.65 (m, 5H, quinoline H); and 8.95–9.40 ppm (m, 2H, quinoline H) |
| 10 | CH₃ | –⁺N-CH₂(isoquinolinium) | 36 | 3.45 and 3.93 (AB, J = 18Hz, 2H, SCH₂); 4.21 (s, 3H, OCH₃); 5.25–6.50 (m, 4H, 3-CH₂ and 2 lactam H); 7.41 (s, 1H, thiazole); 7.95–8.80 (m, 6H, isoquinoline H); and 9.79 ppm (bs, 1H, isoquinoline H) |
| 11 | CH₃ | –⁺N(3-methylpyridinium) | 33 | 2.98 (s, 3H, PyCH₃); 3.52 and 3.71 (AB, J = 19Hz, 2H, SCH₂); 4.24 (s, 3H, OCH₃); 5.35–6.12 (m, 4H, CH₂Py and 2 lactam H); 7.37 (s, 1H, thiazole); 7.79–8.76 (m, 4H, Py) |
| 12 | CH₃ | –⁺N(4-methylpyridinium) | 42 | 2.80 (s, 3H, PyCH₃); 3.45 and 3.85 (AB, J = 19Hz, 2H, SCH₂); 4.25 (s, 3H, OCH₃); 5.15–6.35 (m, 4H, CH₂Py and 2 lactam H); 7.42 (s, 1H, thiazole); and 7.86 and 8.74 (each one d, J = 6Hz, 4 Py—H) |
| 13 | CH₃ | –⁺N(3,5-dimethylpyridinium) | 67 | 2.60 (s, 3H, PyCH₃); 3.63 and 3.86 (AB, J = 19Hz, 2H, SCH₂); 4.24 (s, 3H, OCH₃); 5.15–6.55 (m, 4H, CH₂Py and 2 lactam H); 7.42 (s, 1H, thiazole); and 7.75–9.05 (m, 4H, Py). |
| 14 | CH₃ | –⁺N(4-methylquinolinium/lepidinium) | 19 | 3.15 (s, 3H, CH₃); 3.3 and 3.7 (AB, 2H, SCH₂); 4.25 (s, 3H, OCH₃); 5.1–6.7 (m, 4H, CH₂Py and 2 lactam H); 7.4 (s, 1H, thiazole); and 7.8–9.2 (m, 6H, lepidine) |
| 15 | CH₃ | –⁺N(3-chloropyridinium) | 26 | 3.50 and 3.85 (AB, J = 19Hz, 2H, SCH₂); 4.23 (s, 3H, OCH₃); 5.10–6.42 (m, 4H, CH₂Py and 2 lactam H); 7.40 (s, 1H, thiazole); and 7.90–9.15 (m, 4H, Py) |
| 16 | CH₃ | –⁺N(5,6,7,8-tetrahydroquinolinium) | 68 | 1.7–2.4 (m, 4H, cyclohexene H); 2.7–3.5 (m, 4H, cyclohexene-H); 3.50 and 3.70 (AB, J = 19Hz, 2H, SCH₂); 4.25 (s, 3H, OCH₃); 5.38 (d, J = 5Hz, C₆—H); 5.55 and 5.80 (AB, 2H, CH₂Py); 6.08 (d, J = 5Hz, C₇—H); 7.39 (s, 1H, thiazole); and 7.65–8.58 (m, 3H, Py) |

TABLE 1-continued

Compounds $$\text{H}_2\text{N}-\underset{S}{\overset{N}{\|}}-\overset{C}{\underset{\underset{OR^2}{N}}{\|}}-\text{CONH}-\underset{O}{\overset{S}{\|}}-\underset{CO_2^{\ominus}}{\overset{}{N}}=\text{CH}_2\text{A}$$

| | | | | |
|---|---|---|---|---|
| 17 | CH₃ | —⊕N—⟨pyridyl⟩—C₆H₅ | 55 | 3.55 and 3.83 (AB, J = 19Hz, 2H; SCH₂); 4.20 (s, 3H, OCH₃); 5.20–6.26 (m, 4H, CH₂Py and 2 lactam H); 7.35 (s, 1H, thiazole); 7.51–7.89 (m, 5H, C₆H₅); and 8.26 and 8.91 (AA'BB', J = 7Hz, 4H, Py). |
| 18 | CH₃ | —⊕N—⟨pyridyl⟩—CONH₂ | 50 | 3.60 and 3.83 (AB, J = 18Hz, 2H, SCH₂); 4.22 (s, 3H, OCH₃); 5.33–6.38 (m, 4H, CH₂Py and 2 lactam H); 7.36 (s, 1H, thiazole); and 8.12–9.60 (m, 4H, Py). |
| 19 | CH₃ | —⊕N—⟨pyridyl⟩—CH₂CH₂SO₃K | 17 | 3.4–3.9 (m, 6H, SCH₂ and CH₂CH₂); 4.25 (s, 3H, OCH₃); 5.1–6.25 (m, 4H, CH₂Py and 2 lactam H); 7.38 (s, 1H, thiazole); and 8.12 and 8.79 (AA'BB', J = 6Hz, 4H, Py). |
| 20 | CH₂COOH | —⊕N—⟨cyclopenteno-pyridyl⟩ | 15 | 2.3–2.8 (m, 2H, cyclopentene H); 3.1–4.0 (m, 6H, 4 cyclopentene H and SCH₂); 5.09 (s, 2H, OCH₂); 5.1–6.25 (m, 4H, CH₂Py and 2 lactam H); 7.43 (s, 1H, thiazole); and 7.65–8.65 (m, 3H, Py). |

EXAMPLE 21

7-[2-(2-Amino-5-chlorothiazol-4-yl)-2-syn-methoxyiminoacetamido]-[2,3-cyclopenteno-1-pyridinio)methyl]-ceph-3-em-4-carboxylate The title compound is obtained in 66% yield from 7-[2-(2-amino-5-chlorothiazol-4-yl)-2-syn-methoxyiminoacetamido]-cephalosporanic acid and 2,3-cyclopentenopyridine analogously to Example 1a.

$^1$H—NMR (CF₃CO₂D): δ=2.2–2.8 (m, 2H, cyclopentene H); 3.1–4.2 (m, 6H, 4 cyclopentene H and SCH₂); 4.21 (s, 3H, OCH₃); 5.2–6.2 (m, 4H, CH₂Py and 2 lactam H); 7.6–8.6 (m, 3H, Py).

EXAMPLE 22

7-[2-(5-Amino-1,2,4-thiadiazol-3-yl)-2-syn-methoxyiminoacetamido]-3-[(2,3-cyclopenteno-1-pyridinio)-methyl]-ceph-3-em-4-carboxylate A mixture of 46 mg (0.1 mmole) of 7-[2-(5-amino-1,2,4-thiadiazol-3-yl)-2-syn-methoxyiminoacetamido]-cephalosporanic acid, 0.1 ml (0.85 mmole) of 2,3-cyclopentenopyridine, 0.1 ml (0.7 mmole) of trimethyliodosilane and 1.5 ml of methylene chloride is boiled under reflux for 1.5 hours. The solvent is removed in vacuo, 1.5 ml of ice-water are added to the residue and the solution is chromatographed over a Lobar B prepacked column (Merck, Darmstadt, Cat. No. 10401) using acetone:water (2:1). The product fractions are concentrated and freeze-dried.

Yield: 32 mg (61.6%) of colorless amorphous product.

IR (KBr): 1770 cm⁻¹ (lactam CO)

$^1$H—NMR (CF₃CO₂D): δ=2.25–2.85 (m, 2H, cyclopentene H); 3.1–4.05 (m, 6H, 4 cyclopentene H and SCH₂); 4.30 (s, 3H, OCH₃); 5.2–6.2 (m, 4H, CH₂Py and 2 lactam H); 7.66–8.0 (m, 1py-H); and 8.16–8.7 ppm (m, 2H, Py).

The compounds listed below are obtained in the form of the free bases analogously to variant a of example 1.

TABLE 2 compounds

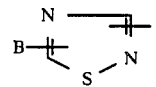

| Example | A | Yield % of theory | $^1$H—NMR(CF$_3$CO$_2$D): δ(ppm) |
|---|---|---|---|
| 23 | 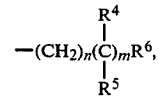 | 52 | 3.45 and 3.85 (AB, J = 19Hz, 2H, SCH$_2$), 4.20 (s, 3H, OCH$_3$); 5.2–6.4 (m, 4H, CH$_2$N and 2 lactam H each having a d at 5.39 and 6.08, J = 5Hz) 7.30 (m, 1H); 7.40 (s, 1H, thiazole); 8.0–8.3 (m, 2H); 8.7–9.0 (m, 1H); 9.43 (bs, 1H/Py) |
| 24 | | 43 | 3.28 (s, 3H, CH$_3$); 3.45 and 3.72 (AB, J = 19Hz, 2H, SCH$_2$) 4.23 (s, 3H, OCH$_3$); 5.25–6.4 (m, 4H, CH$_2$N and 2 lactam H each having a d at 5.40 and 6.08, J = 5Hz); 7.41 (s, 1H, thiazole); 7.6–8.7 m, 4H/Py) |
| 25 | | 82 | 3.48 and 3.81 (AB, J = 19Hz, 2H, SCH$_2$); 4.10 and 4.23 (each having an s, 6H, 2 × OCH$_3$) 5.15–6.40 (m, 4H, CH$_2$N and 2 lactam H); 7.40 (s, 1H, thiazole); 7.9–8.8 (m, 4H, Py) |
| 26 | | 42 | 1.8–2.3 (m, 4H, Cyclohexene-H); 2.7–3.7 (m, 6H, SCH$_2$ and cyclohexene H) 4.22 (s, 3H, OCH$_3$); 5.1–6.4 (m, 4H, CH$_2$N and 2 lactam H); 7.41 (s, 1H, thiazole); 7.6–8.7 (m, 3H, Py) |

We claim:

1. A process for the preparation of a cephem compound of the formula I

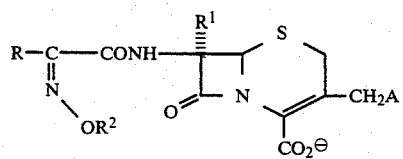

in which R denotes a thiazolyl radical

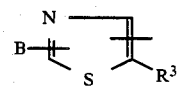

or a 1,2,4-thiadiazolyl radical

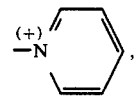

in which
R$^3$ represents hydrogen or halogen and B represents an amino group or an amino group substituted with an amino protective group, and wherein
R$^1$ denotes hydrogen,
R$^2$ denotes hydrogen, C$_1$–C$_6$-alkyl, which can be monosubstituted or polysubstituted by halogen, C$_1$–C$_6$-alkylthio, C$_1$–C$_6$-alkoxy, phenyl or 1,3-thiazol-4-yl or denotes C$_2$–C$_6$-alkenyl, which can be monosubstituted or polysubstituted by halogen; or denotes C$_2$–C$_3$-alkynyl, C$_3$–C$_6$-cycloalkyl, C$_3$–C$_6$-cycloalkyl-C$_1$–C$_6$-alkyl, C$_4$–C$_7$-cycloalkenyl, or the group $$-(CH_2)_n(\underset{R^5}{\overset{R^4}{C}})_m R^6,$$

in which m and n are each 0 or 1,
R$^4$ and R$^5$ can be identical or different and denote hydrogen, phenyl or a C$_1$–C$_4$-alkyl group, or, together with the carbon to which they are bonded, form a methylene or C$_3$–C$_7$-cycloalkylidene group, R$^6$ denotes a COOH, CN or CONH$_2$ group, it being possible for the latter to be monosubstituted or disubstituted on the nitrogen by methyl or ethyl, A denoes a quinolinium or isoquinolinium radical, each of which can also be monosubstituted or polysubstituted by identical or different substituents from the group comprising
C$_1$–C$_6$-alkyl, which can be substituted by hydroxyl; halogen,
trifluoromethyl and
hydroxyl,
or denotes a pyridinium radical $$\underset{-N}{\overset{(+)}{\diagdown}}\diagup$$

which can be monosubstituted or polysubstituted by identical or different substituents from the group comprising C$_1$–C$_6$-alkyl, which can be monosubstituted or polysubstituted by hydroxyl; formyl and C$_1$–C$_6$-alkylcarbonyl, sulfo, carbamoyl, C$_1$–C$_6$-alkoxy and hydroxy-C$_1$–C$_6$-alkoxy, it also being possible for 2 neighbouring alkyl groups to be linked to form a tri- to pentamethylene ring in which one ring carbon atom can be replaced by an oxygen or sulfur atom and which can furthermore also contain one or two double bonds, and which may be substituted by C$_1$–C$_6$-alkyl, C$_1$–C$_4$-alkoxy, hydroxymethyl, halogen, hydroxyl, oxo or exomethylene, C$_2$–C$_6$-alkenyl, which can be substituted by hydroxyl, C$_2$–C$_6$-alkynyl,
C$_3$–C$_7$-cycloalkyl and C$_3$–C$_7$-cycloalkylmethyl, it being possible for the ring in these two substituents also to be substituted by hydroxyl or halogen,
C$_4$–C$_7$-cycloalkenyl,
C$_1$–C$_6$-alkoxy, which can be substituted by hydroxyl, $C_2$–$C_6$-alkenyloxy and $C_2$–$C_6$-alkynyloxy, halogen, trifluoromethyl and hydroxyl; phenyl, benzyl which can also be substituted by halogen, 2′-thienyl or 3′-thienyl, formyl, $C_1$–$C_6$-alkylcarbonyl, which can also be substituted by hydroxyl, phenylcarbonyl and carbamoyl, and in which the $R^2O$ group is in the syn-position, which comprises reacting a compound of the formula II

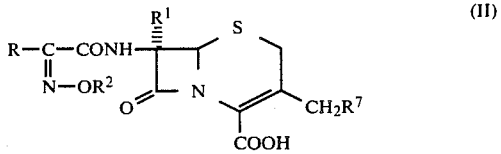

or salts thereof, in which R, $R^1$ and $R^2$ have the meaning given for formula I and $R^7$ denotes a group which can be replaced by the base corresponding to the radicals A of formula I, with a molar excess of this base in the presence of a tri-$C_1$–$C_4$-alkyliodosilane to form a compound of the formula I and said base is also present in molar excess related to said tri-$C_1$–$C_4$-alkyliodosilane and (a) splitting off any protective group present and
(b) if necessary, converting the resulting product into a physiologically acceptable acid addition salt.

2. The process as claimed in claim 3, wherein the tri-$C_1$–$C_4$-alkyliodosilane is trimethyl- or triethyliodosilane.

* * * * *

UNITED STATES PATENT AND TRADEMARK OFFICE
CERTIFICATE OF CORRECTION

PATENT NO. : 4,692,516

DATED : September 8, 1987

INVENTOR(S) : Reiner Kirrstetter, et al.

It is certified that error appears in the above-identified patent and that said Letters Patent is hereby corrected as shown below:

In claim 1, Column 18, Line 32; change:

"denoes" to --denotes--.

Signed and Sealed this

Twenty-third Day of February, 1988

Attest:

DONALD J. QUIGG

Attesting Officer     Commissioner of Patents and Trademarks